(12) United States Patent
Sato

(10) Patent No.: US 9,113,811 B2
(45) Date of Patent: Aug. 25, 2015

(54) IMAGE PROCESSING APPARATUS AND COMPUTER PROGRAM PRODUCT

(75) Inventor: Takeshi Sato, Nasushiobara (JP)

(73) Assignees: Toshiba Medical Systems Corporation, Otawara-shi (JP); Kabushiki Kaisha Toshiba, Tokyo (JP)

(*) Notice: Subject to any disclaimer, the term of this patent is extended or adjusted under 35 U.S.C. 154(b) by 600 days.

(21) Appl. No.: 12/464,472

(22) Filed: May 12, 2009

(65) Prior Publication Data

US 2009/0292206 A1  Nov. 26, 2009

(30) Foreign Application Priority Data

May 20, 2008 (JP) ................................. 2008-131834

(51) Int. Cl.
*A61B 8/00* (2006.01)
*A61B 8/06* (2006.01)
*A61B 8/13* (2006.01)
(Continued)

(52) U.S. Cl.
CPC ... *A61B 8/06* (2013.01); *A61B 8/13* (2013.01); *A61B 8/483* (2013.01); *G06T 15/08* (2013.01); *G06T 19/00* (2013.01); *G06T 2210/24* (2013.01); *G06T 2210/41* (2013.01)

(58) Field of Classification Search
USPC ......... 600/322, 326, 407, 437, 438, 442, 443, 600/445, 454, 456, 463; 345/418, 419, 420, 345/424, 581, 589, 597, 598
See application file for complete search history.

(56) References Cited

U.S. PATENT DOCUMENTS 5,394,874 A * 3/1995 Forestieri et al. ............. 600/441
5,497,776 A * 3/1996 Yamazaki et al. ............. 600/445

(Continued)

FOREIGN PATENT DOCUMENTS

JP  2-305559 A  12/1990
JP  3-269679 A  12/1991
(Continued)

OTHER PUBLICATIONS

"The Language of Technical Computing", MATLAB, Using MATLAB Graphics, Version 7, The MathWorks, chpter 16—Volume Visulization Techniques, (2004), 3 pages (16-40, 16-41).
(Continued)

*Primary Examiner* — Unsu Jung
*Assistant Examiner* — Michael N Fisher
(74) *Attorney, Agent, or Firm* — Oblon, McClelland, Maier & Neustadt, L.L.P.

(57) ABSTRACT

A tissue-image creating unit creates a tissue image including depth values by volume rendering from three-dimensional tissue data stored in a three-dimensional data storage unit. A blood-flow data converting unit scatters a blood flow in three-dimensional blood-flow data stored in the three-dimensional data storage unit into particles, and converts the three-dimensional blood-flow data into three-dimensional particle data. A blood-flow image creating unit creates a blood-flow image including depth values from the three-dimensional particle data. A composite-image creating unit then creates a composite image by coordinating the order of rendering particles and tissue based on the depth values of respective pixels included in the tissue image and the depth values of respective particles included in the blood-flow image. A display control unit then controls display of the composite image so as to be displayed in order onto a monitor included in an output unit.

11 Claims, 13 Drawing Sheets

(51) Int. Cl.
*G06T 19/00* (2011.01)
*G06T 15/08* (2011.01)
*A61B 8/08* (2006.01)

(56) References Cited

U.S. PATENT DOCUMENTS

| | | | | |
|---|---|---|---|---|
| 5,608,849 | A | * | 3/1997 | King, Jr. .................. 345/419 |
| 5,776,067 | A | * | 7/1998 | Kamada et al. ............. 600/443 |
| 6,208,883 | B1 | * | 3/2001 | Holupka et al. ............. 600/407 |
| 6,256,529 | B1 | * | 7/2001 | Holupka et al. ............. 600/427 |
| 6,464,642 | B1 | | 10/2002 | Kawagishi |
| 6,498,607 | B1 | * | 12/2002 | Pfister et al. ................. 345/423 |
| 2003/0125624 | A1 | | 7/2003 | Shiki |
| 2006/0050963 | A1 | * | 3/2006 | Suzuki et al. ............... 382/190 |
| 2007/0255138 | A1 | * | 11/2007 | Kristofferson et al. ....... 600/443 |
| 2008/0077013 | A1 | | 3/2008 | Kawagishi et al. |

FOREIGN PATENT DOCUMENTS

| | | | |
|---|---|---|---|
| JP | 5-92001 | A | 4/1993 |
| JP | 9-262236 | A | 10/1997 |
| JP | 2007-296333 | | 11/2007 |
| JP | 2008-73279 | A | 4/2008 |
| WO | WO 2008/008936 | A2 | 1/2008 |

OTHER PUBLICATIONS

Office Action issued Jun. 28, 2011, in European Patent Application No. 09 006 615.0.

"Dot Distribution Maps", Wikipedia, http://en.wikipedia.org/wiki/Dot_Distribution_Maps, Jun. 6, 2011, 4 pages.

Charles A. Taylor, et al., "Finite element modeling of blood flow in arteries", Computer Methods in Applied Mechanics and Engineering, vol. 158, 1998, pp. 155-196.

Japanese Office Action issued Jun. 11, 2013 in Patent Application No. 2009-080121 with English Translation.

Anonymous, "Volume Visualization Techniques", MATLAB (the Language of Technical Computing)—Using MATLAB Graphics, Version 6, Chapter 15, XP-002543843, pp. 1-46 and two additional pages.

* cited by examiner

TISSUE IMAGE INCLUDING DEPTH VALUES

BLOOD FLOW

BLOOD FLOW IS PRESENT

ARRANGEMENT OF PARTICLE

BLOOD-FLOW IMAGE INCLUDING DEPTH VALUES

VARY BRIGHTNESS OF PARTICLES IN ACCORDANCE WITH BLOOD-FLOW INFORMATION (VELOCITY, DISPERSION, POWER)

VARY SIZES OF PARTICLES IN ACCORDANCE WITH BLOOD-FLOW INFORMATION (VELOCITY, DISPERSION, POWER)

VARY ARRANGEMENT DENSITIES OF PARTICLES IN ACCORDANCE WITH BLOOD-FLOW INFORMATION (VELOCITY, DISPERSION, POWER)

CHANGE ARRANGEMENT OF PARTICLE

CHANGE ARRANGEMENT OF PARTICLE IN
ACCORDANCE WITH VELOCITY OR DISPERSION

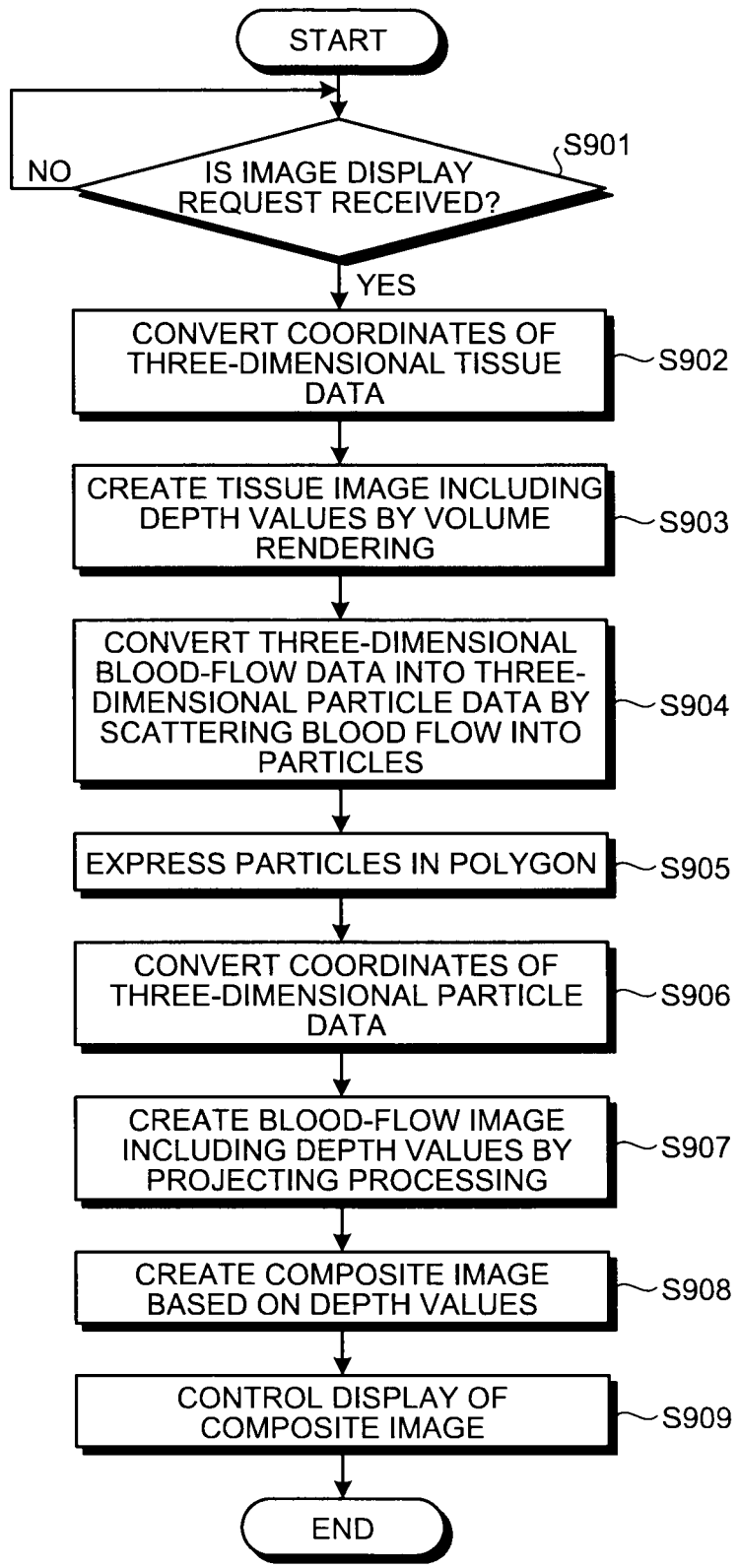

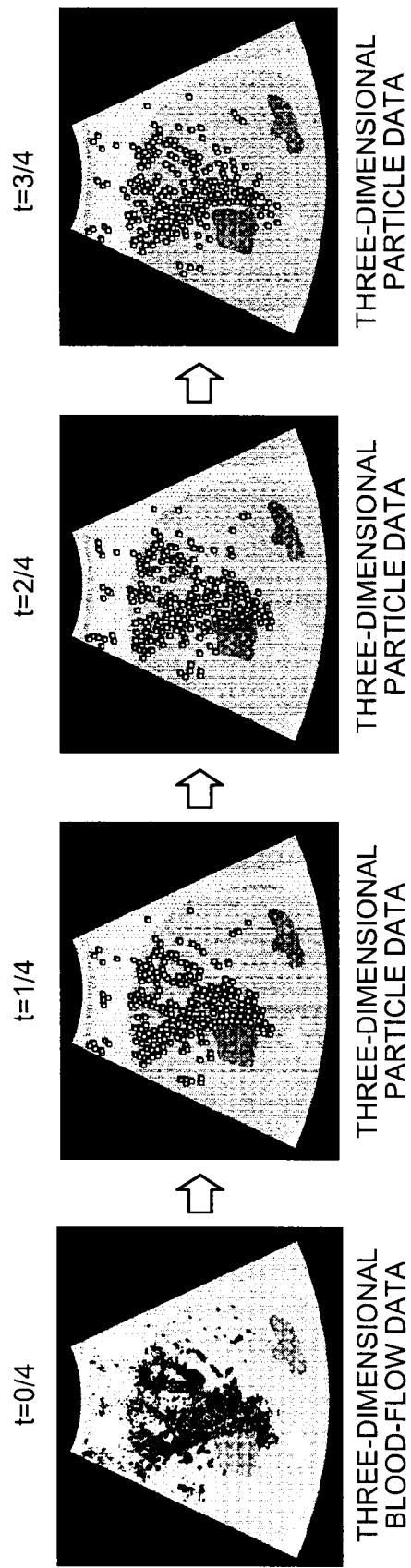

IMAGE PROCESSING APPARATUS AND COMPUTER PROGRAM PRODUCT

CROSS-REFERENCE TO RELATED APPLICATIONS

This application is based upon and claims the benefit of priority from the prior Japanese Patent Application No. 2008-131834, filed on May 20, 2008; the entire contents of which are incorporated herein by reference.

BACKGROUND OF THE INVENTION

1. Field of the Invention

The present invention relates to an image processing apparatus and a computer program product.

2. Description of the Related Art

Conventionally, an ultrasonic diagnostic apparatus is used in a medical practice of today for an examination of and a diagnosis on various living body tissues, such as a heart, a liver, a kidney, and a mammary gland, as an apparatus that has advantages, such as simple to operate, noninvasive, and without risk of radiation exposure, compared with other medical image diagnostic apparatuses, for example, an X-ray diagnostic apparatus, and an X-ray Computed Tomography (CT) apparatus.

An ultrasonic diagnostic apparatus transmits an ultrasonic wave from an ultrasonic probe, and receives an ultrasonic wave reflected from internal tissue of a subject, thereby creating a tomogram (B-mode image) of histology inside the subject in real time. Furthermore, the ultrasonic diagnostic apparatus creates blood-flow information as a Doppler image in real time by using the Doppler effect of ultrasonic waves, the blood-flow information including, for example, an area in which a blood flow is present inside a subject, and the velocity, dispersion (disturbance in the blood flow) and power (diffusion strength of the blood flow) of the blood flow.

Recently, an ultrasonic diagnostic apparatus has come into practical use, which creates a three-dimensional ultrasonic image in real time by scanning three-dimensionally the inside of a subject by using a two-dimensional array transducer ultrasonic probe. The ultrasonic diagnostic apparatus that performs a three-dimensional scan can collect in real time, for example, a B-mode image of three-dimensional histology of a heart that is beating time-sequentially, and can display the B-mode image.

When displaying the three-dimensional B-mode image, a method of volume rendering is used. For example, the histology of a heart includes a heart wall and a heart valve to be depicted with high brightness in a B-mode image, and a heart cavity of which almost all part of the inside is to be depicted in black. Accordingly, by volume-rendering a half of the heart as a display subject region, a stereoscopic image of the heart wall and/or the heart valve viewed from the inside of the heart cavity can be displayed. By referring to a stereoscopic image of a half of a heart that is volume-rendered, a doctor can efficiently diagnose a disease in a heart valve or a heart wall, or congenital anomaly in the heart valve or the heart wall.

The ultrasonic diagnostic apparatus that performs a three-dimensional scan can simultaneously collect three-dimensional information about a blood flow with three-dimensional information about histology by using the Doppler effect, and can display a three-dimensional blood-flow distribution by performing volume rendering on a three-dimensional Doppler image.

For example, when performing volume rendering on a three-dimensional Doppler image, three-dimensionally highlighted turbulence in a blood flow can be rendered by using dispersion of blood-flow velocities in blood-flow information (for example, see JP-A 2007-296333 (KOKAI)), accordingly, a turbulent blood flow caused by anomaly in a hear wall or a heart valve can be clearly displayed.

According to the above conventional technology, there is a problem that a blood flow cannot be displayed in three dimensions in a format suitable for diagnosis.

For example, blood is filled in a heart cavity of the heart, and the velocity of a blood flow continuously changes, as a result, a region in which the blood flow is present does not have clear border. For this reason, when performing volume rendering on a three-dimensional Doppler image, the blood flow cannot be stereoscopically displayed.

For a doctor to perform diagnosis efficiently, information about histology is needed simultaneously with blood-flow information; however, if a three-dimensional B-mode image on which volume rendering is performed is displayed in a superposed manner over a three-dimensional Doppler image on which volume rendering is performed, histology behind a blood flow is hidden. For this reason, the information about histology cannot be clearly displayed along with the blood-flow information.

As described above, according to the conventional technology, although a turbulent blood flow caused by anomaly in a heart valve or a heart wall can be clearly displayed, three-dimensional information about the blood flow cannot be displayed in a format suitable for diagnosis as well as three-dimensional information about histology.

SUMMARY OF THE INVENTION

According to an aspect of the present invention, there is provided an image processing apparatus includes an image creating unit that acquires three-dimensional histology information about tissue inside a subject and three-dimensional fluid information about fluid moving inside the subject both of which are created based on a reflection wave of an ultrasonic wave transmitted to the inside of the subject, creates three-dimensional particle information converted from the three-dimensional fluid information by arranging a plurality of particles in three dimensions in a scattered manner in an area in which the fluid is present in the three-dimensional fluid information, and creates a composite image based on created three-dimensional particle information and the three-dimensional histology information and a display control unit (16) that controls display of the composite image created by the image creating unit (14) so as to be displayed onto a predetermined display unit.

According to another aspect of the present invention, there is provided a computer program product having a computer readable medium including programmed instructions for processing an image, wherein the instructions, when executed by a computer, cause the computer to perform acquiring three-dimensional histology information about tissue inside a subject and three-dimensional fluid information about fluid moving inside the subject both of which are created based on a reflection wave of an ultrasonic wave transmitted to the inside of the subject, creating three-dimensional particle information converted from the three-dimensional fluid information by arranging a plurality of particles in three dimensions in a scattered manner in an area in which the fluid is present in the three-dimensional fluid information, and creating a composite image based on created three-dimensional particle information and the three-dimensional histology information and controlling display of the composite image so as to be displayed onto a predetermined display unit.

BRIEF DESCRIPTION OF THE DRAWINGS

FIG. 9 is a flowchart for explaining processing performed by the image processing apparatus according to the first embodiment;

FIG. 13 is a schematic diagram for explaining a composite-image creating unit according to the third embodiment.

DETAILED DESCRIPTION OF THE INVENTION

Exemplary embodiments of an image processing apparatus and a computer program product of the present invention will be explained below in detail with reference to the accompanying drawings.

Figure 1:
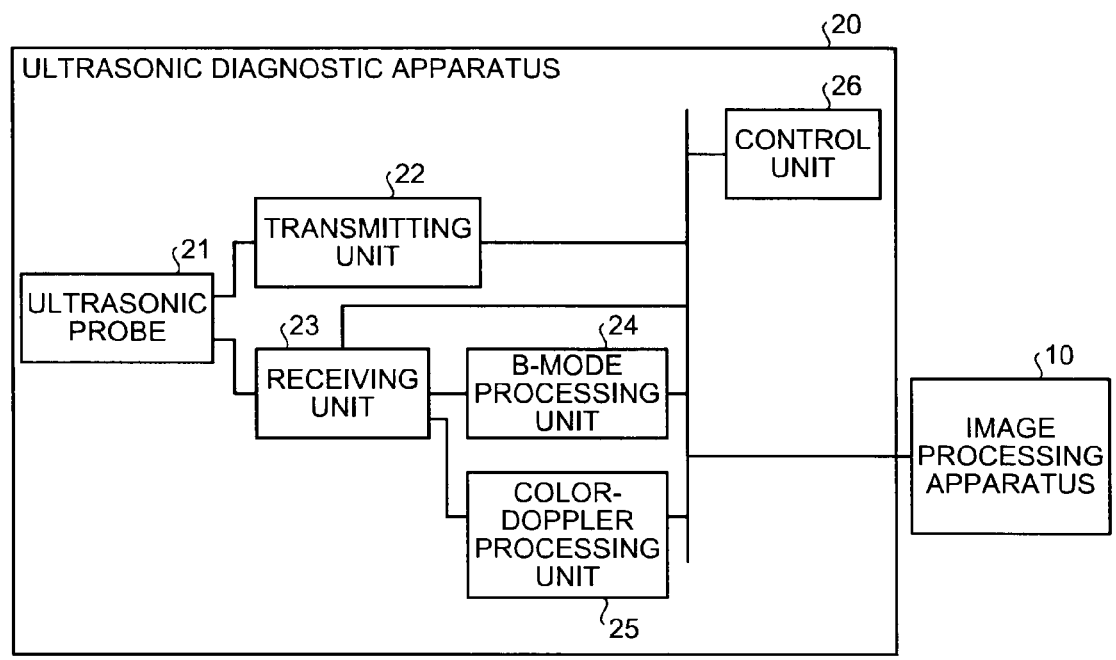
FIG. 1 is a functional block diagram for explaining a configuration of an ultrasonic diagnostic apparatus configured to be connected to an image processing apparatus according to a first embodiment of the present invention.

First of all, a configuration of an ultrasonic diagnostic apparatus configured to be connected to an image processing apparatus according to a first embodiment of the present invention is explained below. FIG. 1 is a functional block diagram for explaining a configuration of the ultrasonic diagnostic apparatus configured to be connected to the image processing apparatus according to the first embodiment.

As shown in FIG. 1, an ultrasonic diagnostic apparatus 20 to be connected to the image processing apparatus according to the first embodiment includes an ultrasonic probe 21, a transmitting unit 22, a receiving unit 23, a B-mode processing unit 24, a color-Doppler processing unit 25, and a control unit 26.

The ultrasonic probe 21 is a two-dimensional array transducer ultrasonic probe that includes built-in ultrasonic transducers arranged in matrix, transmits a ultrasonic wave generated by the ultrasonic transducers into the inside of a subject, and receives a reflected wave from internal tissue of the subject, thereby scanning three-dimensionally the inside of the subject.

The transmitting unit 22 is connected to the ultrasonic probe 21, generates a high-voltage pulse on each predetermined delay time in accordance with the control of the control unit 26, which will be described later, and applies the generated high-voltage pulse to the ultrasonic transducers built-in the ultrasonic probe 21 in order. Accordingly, the ultrasonic probe 21 generates an ultrasonic wave.

The receiving unit 23 is connected to the ultrasonic probe 21, performs gain-correction processing and analog-to-digital (A/D) converting processing upon receiving input of a received signal of a reflected wave received by the ultrasonic probe 21.

The B-mode processing unit 24 performs creation processing for three-dimensional tissue data to be used for depicting a structure of tissue inside the subject as a three-dimensional B-mode image based on received data received and created by the receiving unit 23. Three-dimensional tissue data corresponds to "three-dimensional histology information" described in the accompanying claims.

The color-Doppler processing unit 25 performs creation processing for three-dimensional blood-flow data to be used for depicting blood-flow information, for example, an area in which a blood flow moving inside a subject is present, and the velocity, dispersion (disturbance in the blood flow) and power (diffusion strength of the blood flow) of the blood flow, as a three-dimensional color-Doppler image by using received data created and received by the receiving unit 23 and the Doppler effect of ultrasonic waves. Blood flow corresponds to "fluid" described in the accompanying claims, and three-dimensional blood-flow data corresponds to "three-dimensional fluid information" similarly.

The control unit 26 controls the transmitting unit 22, the receiving unit 23, the B-mode processing unit 24, and the color-Doppler processing unit 25 based on setting conditions received via a not-shown input unit from an operator of the ultrasonic diagnostic apparatus 20. Specifically, the control unit 26 controls the transmitting unit 22, the receiving unit 23, the B-mode processing unit 24, and the color-Doppler processing unit 25, based on setting conditions, for example, a delay time of a high-voltage pulse to be generated by the transmitting unit 22, timing of transmitting and receiving of received data between the receiving unit 23 and the B-mode processing unit 24, and timing of transmitting and receiving of received data between the receiving unit 23 and the color-Doppler processing unit 25.

An image processing apparatus 10 displays an image created by using three-dimensional tissue data created by the B-mode processing unit 24 and three-dimensional blood-flow data created by the color-Doppler processing unit 25, and has a main feature that a blood flow can be displayed in three dimensions in a format suitable for diagnosis.

Figure 2:
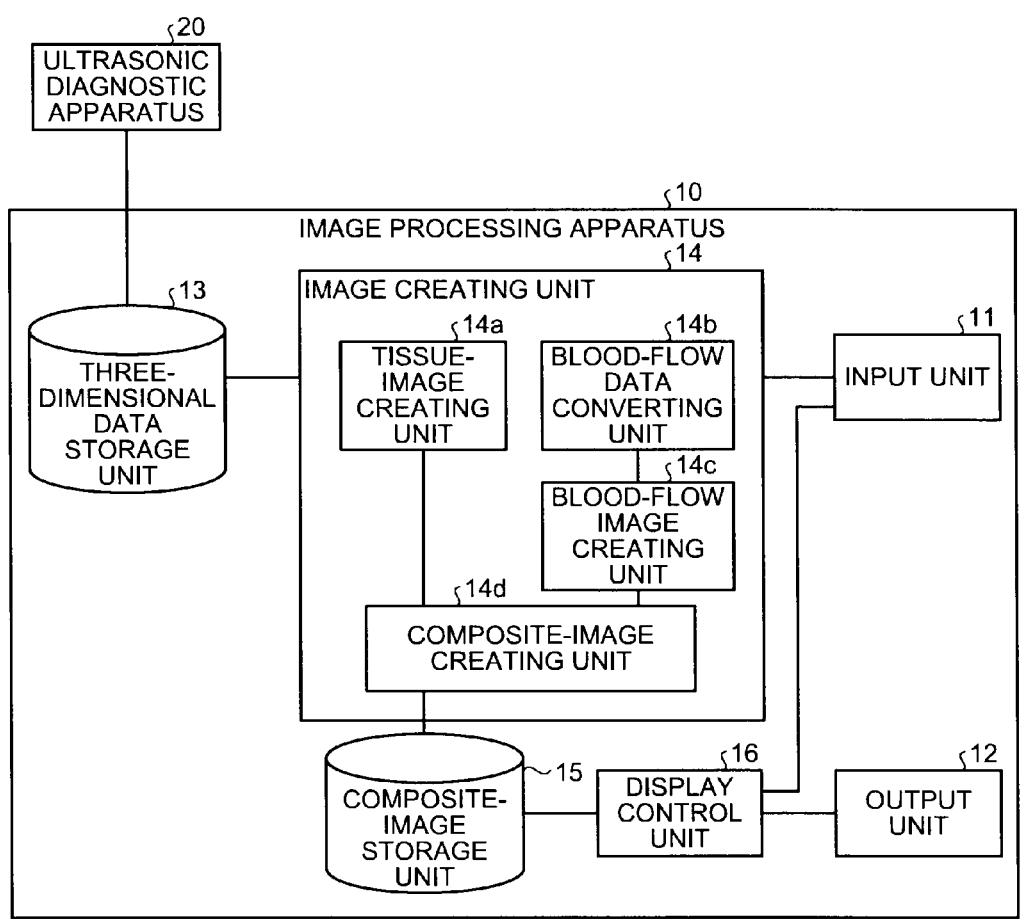
FIG. 2 is a functional block diagram for explaining a configuration of the image processing apparatus according to the first embodiment.
Figure 3:
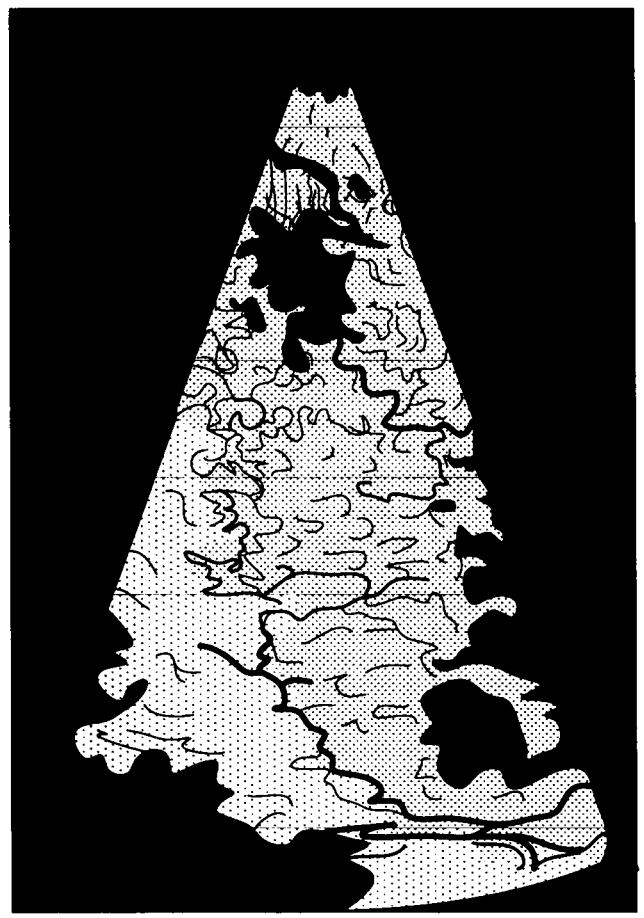
FIG. 3 is a schematic diagram for explaining a tissue-image creating unit shown in FIG. 2.
Figure 4A:
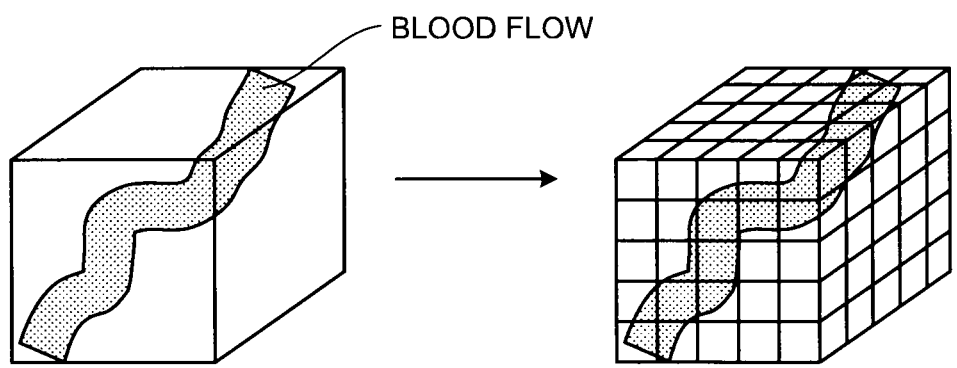
FIG. 4 is a schematic diagram for explaining a blood-flow data converting unit shown in FIG. 2.
Figure 4B:
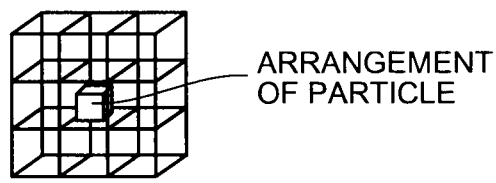
Figure 5:
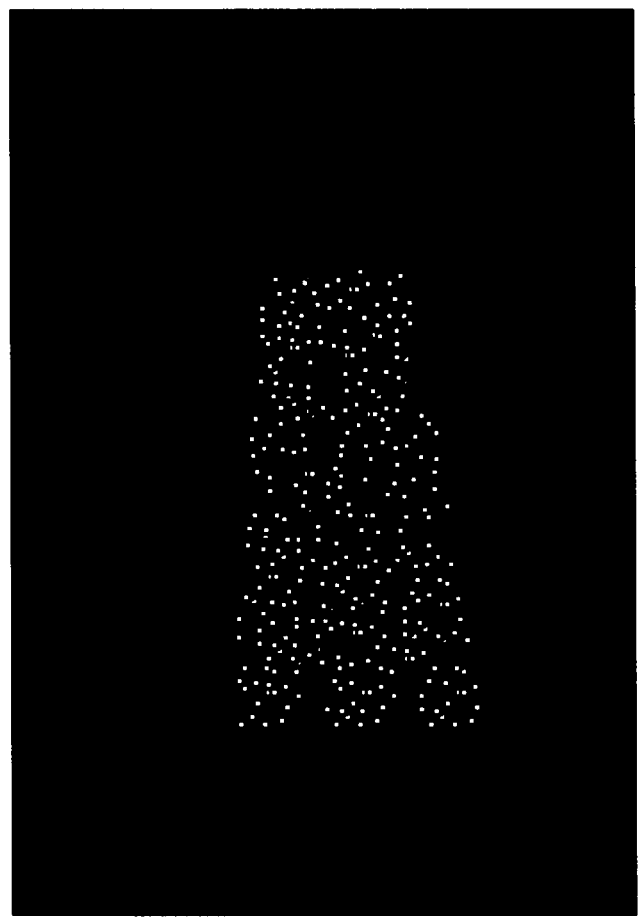
FIG. 5 is a schematic diagram for explaining a blood-flow image creating unit shown in FIG. 2.
Figure 6:
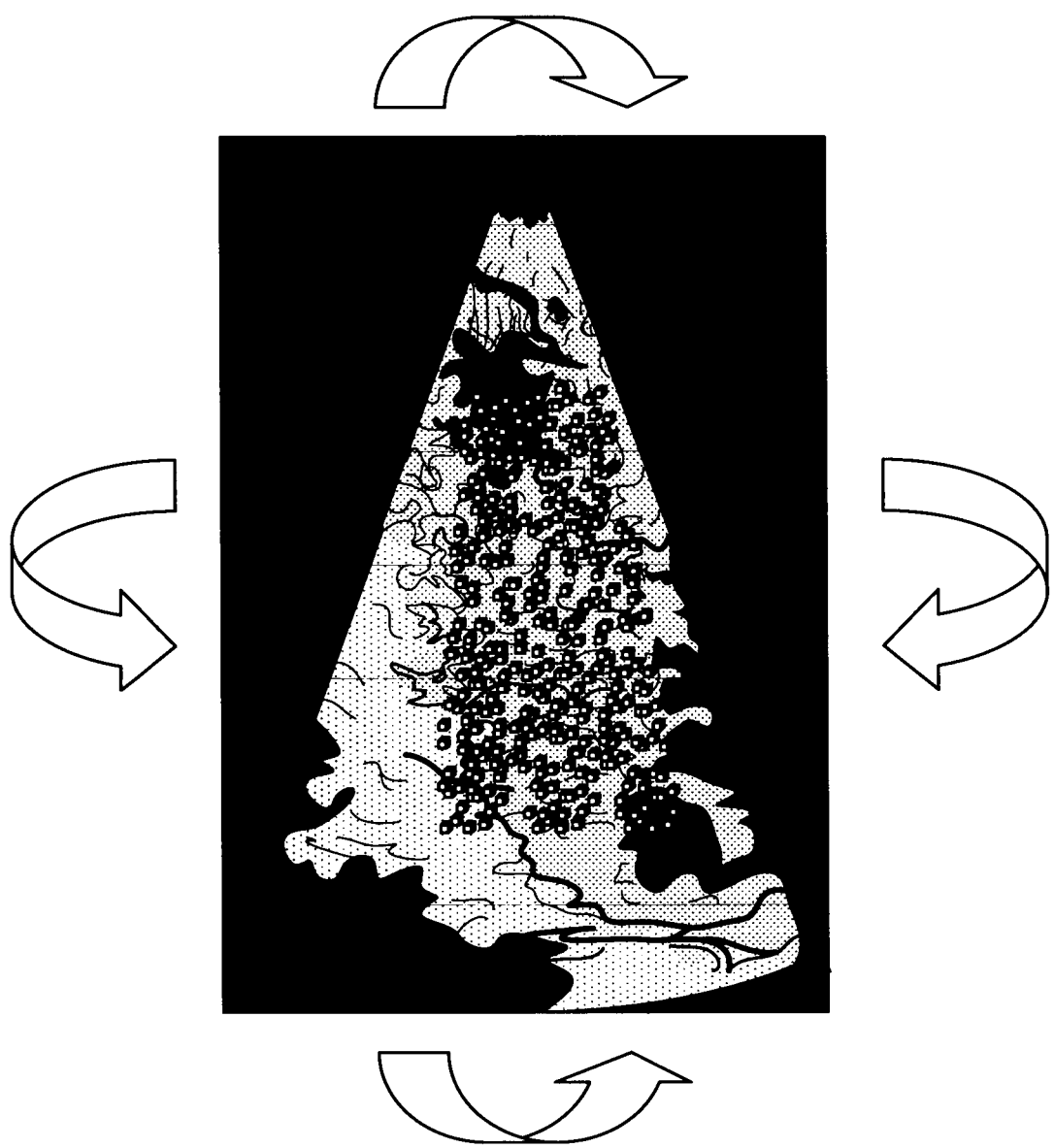
FIG. 6 is a schematic diagram for explaining a composite-image creating unit according to the first embodiment.

The main feature is explained below with reference to FIGS. 2 to 6. FIG. 2 is a functional block diagram for explaining a configuration of the image processing apparatus according to the first embodiment; FIG. 3 is a schematic diagram for explaining a tissue-image creating unit; FIG. 4 is a schematic diagram for explaining a blood-flow data converting unit; FIG. 5 is a schematic diagram for explaining a blood-flow image creating unit; and FIG. 6 is a schematic diagram for explaining a composite-image creating unit according to the first embodiment.

As shown in FIG. 2, the image processing apparatus 10 according to the first embodiment is connected to the ultrasonic diagnostic apparatus 20, and includes an input unit 11, an output unit 12, a three-dimensional data storage unit 13, an image creating unit 14, a composite-image storage unit 15, and a display control unit 16.

The input unit 11 receives input of various information and includes, for example, a mouse and a keyboard; and as particularly closely relevant to the present invention, the input unit 11 receives input of an image display request from an operator of the image processing apparatus 10 (for example, a doctor who interprets an image based on data created by the ultrasonic diagnostic apparatus 20, and performs diagnosis). Moreover, the input unit 11 receives input of a display-subject region setting request from the operator of the image processing apparatus 10.

The output unit 12 outputs various information and includes, for example, a monitor and/or a speaker; and as particularly closely relevant to the present invention, the output unit 12 displays onto the monitor a composite image created by the image creating unit 14, which will be described later, under the control of the display control unit 16, which will be described later.

The three-dimensional data storage unit 13 stores three-dimensional tissue data and three-dimensional blood-flow data created by the ultrasonic diagnostic apparatus 20.

When receiving an image display request and a display-subject region setting request from the operator of the image processing apparatus 10 via the input unit 11, the image creating unit 14 creates a composite image based on three-dimensional tissue data and three-dimensional blood-flow data stored by the three-dimensional data storage unit 13. As shown in FIG. 2, the image creating unit 14 includes a tissue-image creating unit 14a, a blood-flow data converting unit 14b, a blood-flow image creating unit 14c, and a composite-image creating unit 14d.

The tissue-image creating unit 14a creates a tissue image as a B-mode image that depicts a structure of tissue inside the subject in three dimensions from three-dimensional tissue data stored by the three-dimensional data storage unit 13. Specifically, the tissue-image creating unit 14a converts three-dimensional tissue data expressed in a polar coordinate system into data in a rectangular coordinate system, and creates a tissue image by volume-rendering a region corresponding to the display-subject region setting request in the three-dimensional tissue data converted into the rectangular coordinate system.

Moreover, along with creating the tissue image, the tissue-image creating unit 14a acquires positional information in three dimensions in the three-dimensional tissue data about each of pixels included in the created tissue image. Specifically, the tissue-image creating unit 14a acquires a depth value that expresses the depth of each of pixels on the created tissue image, and stores the acquired depth value of each pixel onto the created tissue image.

For example, as shown in FIG. 3, the tissue-image creating unit 14a converts three-dimensional tissue data created based on reflected waves from the heart of the subject into data in the rectangular coordinate system, creates a tissue image of a heart wall or a heart valve viewed from the inside of the heart cavity by volume-rendering a region corresponding to a half of the heart in the three-dimensional tissue data converted into the rectangular coordinate system, and then stores depth values of respective pixels onto the created tissue image.

Returning to FIG. 2, the blood-flow data converting unit 14b creates three-dimensional particle data converted from three-dimensional blood-flow data stored by the three-dimensional data storage unit 13 by arranging a plurality of particles in three dimensions in a scattered manner in an area in which a blood flow is present according to the three-dimensional blood-flow data. Three-dimensional particle data corresponds to "three-dimensional particle information" described in the accompanying claims.

For example, as shown on the left of the section (A) in FIG. 4, the blood-flow data converting unit 14b extracts an area in which a blood flow is present according to the three-dimensional blood-flow data. As shown on the right of the section (A) in FIG. 4, the blood-flow data converting unit 14b then divides the three-dimensional blood-flow data into cubes in a predetermined size, and extracts cubes in each of which the blood flow is present.

The blood-flow data converting unit 14b then creates three-dimensional particle information converted from three-dimensional fluid information by arranging a particle in an extracted cube. For example, as shown in the section (B) in FIG. 4, the blood-flow data converting unit 14b selects a cube arranged in the center of an aggregation of the extracted cubes in which "the blood flow is present", and creates three-dimensional particle information converted from the three-dimensional fluid information by arranging into the cube a reduced cube of which size is reduced (for example, reduced to 50%) from the size of the cube.

Returning to FIG. 2, the blood-flow image creating unit 14c creates a blood-flow image that depicts blood-flow information inside the subject with a plurality of particles arranged in three dimensions in a scattered manner by using the three-dimensional particle data created by the blood-flow data converting unit 14b. Specifically, the blood-flow image creating unit 14c expresses particles in the three-dimensional particle data in a polygon model, and then converts the three-dimensional particle data expressed in the polar coordinate system into data in the rectangular coordinate system. The blood-flow image creating unit 14c then creates a blood-flow image by creating a projection image of a region corresponding to the display-subject region setting request in the three-dimensional particle data converted into the rectangular coordinate system.

Moreover, along with creating the blood-flow image, the blood-flow image creating unit 14c acquires positional information in three dimensions in the three-dimensional particle data about each of the particles included in the created blood-flow image. Specifically, the blood-flow image creating unit 14c acquires a depth value that indicates the depth of each of the particles in the created blood-flow image, and stores the acquired depth value of each particle onto the created blood-flow image.

For example, as shown in FIG. 5, the blood-flow image creating unit 14c creates a blood-flow image viewed from the inside of the heart cavity by creating a projection image from a region corresponding to a half of the heart in the three-dimensional particle data converted into the rectangular coordinate system, and stores depth values of respective particles onto the created blood-flow image.

Returning to FIG. 2, the composite-image creating unit 14d creates a composite image that the tissue image created by the tissue-image creating unit 14a is combined with the blood-flow image created by the blood-flow image creating unit 14c. When creating the composite image, the composite-image creating unit 14d creates the composite image by coordinating the order of rendering particles and tissue based on depth values of pixels included in the tissue image and depth values of particles included in the blood-flow image.

In other words, the composite-image creating unit 14d determines superposition in the depth direction of a tissue and a blood flow expressed in particles based on the depth values of the respective pixels and the depth values of the respective particles, and then creates a composite image by coordinating so as to render priorly a particle or a tissue that is located in front. For example, as shown in FIG. 6, the composite-image creating unit 14d creates a composite image on which a blood flow is expressed in particles as well as histology of the heart of the subject viewed from the inside of the heart cavity, based on the depth values.

The composite-image creating unit 14d then stores the created composite image into the composite-image storage unit 15.

The display control unit 16 reads a composite image stored by the composite-image storage unit 15, and controls display of the read composite image so as to be displayed onto the monitor included in the output unit 12. Moreover, the display control unit 16 controls display of the read image so as to be displayed in a turned manner as shown in FIG. 6, based on a turn display request for the composite image received via the input unit 11.

In this way, by referring to a composite image combined from a tissue image and a blood-flow image that depicts a blood flow as particles, the operator of the image processing apparatus 10 (for example, a doctor who interprets an image taken by the ultrasonic diagnostic apparatus 20, and performs diagnosis) can observe a blood-flow distribution or histology hidden behind a blood flow present in the front.

According to the first embodiment, explained above is a case where the composite-image creating unit 14d creates a composite image that reflects the depth direction of the blood flow and the histology based on depth values of respective pixels included in the tissue image and depth values of respective particles included in the blood-flow image, however, the present invention is not limited to this. For example, the composite-image creating unit 14d can create a composite image on which a blood-flow distribution and histology hidden behind a blood flow present in the front can be observed, by increasing the transparency of the blood-flow image, without using depth value.

Moreover, according to the first embodiment, a case of expressing a blood flow by using a cube as a particle is explained above; however, the present invention is not limited to this, and can be applied to a case of expressing a blood flow by using a particle having an arbitrary shape, such as a column or a sphere.

Figure 7A:
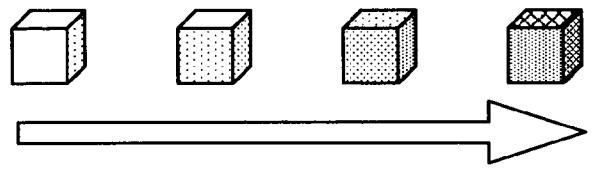
FIG. 7 is a schematic diagram for explaining first, second, and third modifications of processing performed by an image creating unit shown in FIG. 2.
Figure 7B:
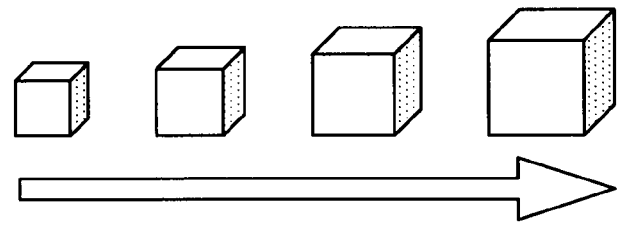
Figure 7C:
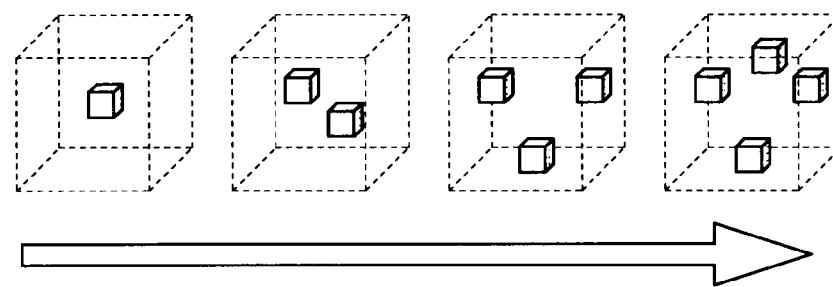
Figure 8A:
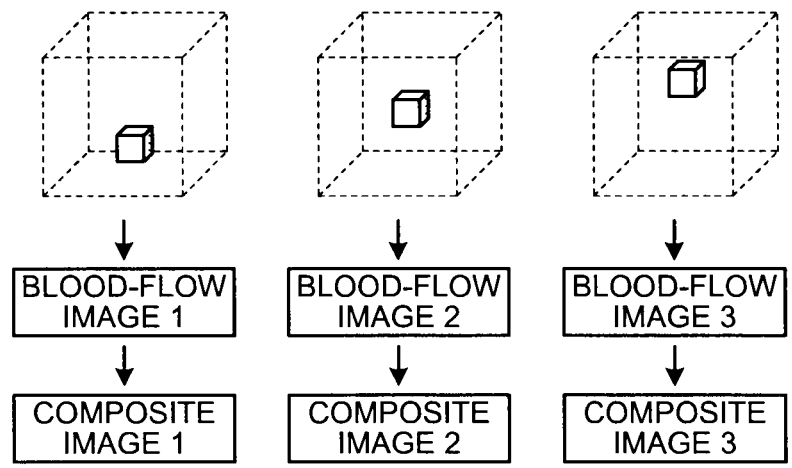
FIG. 8 is a schematic diagram for explaining fourth and fifth modifications of the processing performed by the image creating unit.
Figure 8B:
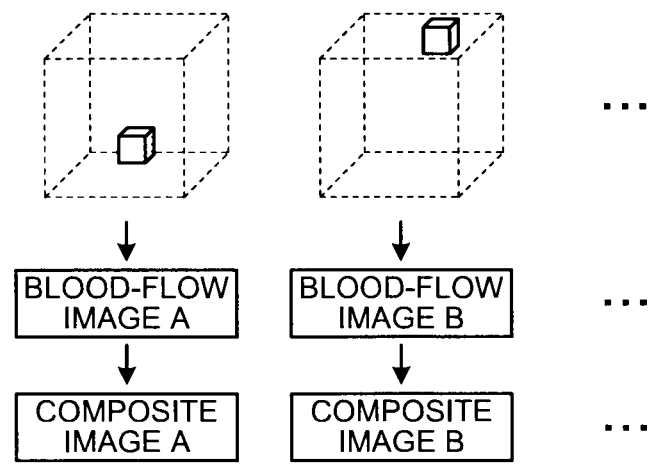

Furthermore, explained above is a case where a blood-flow image is created by using only information about an area in which a blood flow is present from among information included in the three-dimensional blood-flow data; however, the present invention is not limited to this, and can be applied to a case of creating a blood-flow image that also reflects blood-flow information included in the three-dimensional blood-flow data, such as the velocity, dispersion, and power of the blood flow. Five modifications of the processing to be performed by the image creating unit 14 are explained below with reference to FIGS. 7 and 8. FIG. 7 is a schematic diagram for explaining first, second, and third modifications of the processing performed by the image creating unit; and FIG. 8 is a schematic diagram for explaining fourth and fifth modifications of the processing performed by the image creating unit.

Firstly, the blood-flow image creating unit 14c determines the color of a particle in three-dimensional particle data based on the velocity of a blood flow, and/or the dispersion of velocities of the blood flow, and/or the power of the blood flow.

Precisely, the blood-flow image creating unit 14c varies the brightness of the color of particles in accordance with the blood-flow information (velocity, dispersion, and power), as shown in the section (A) in FIG. 7. For example, the blood-flow image creating unit 14c draws a two-dimensional color map so as to express the larger the velocity in absolute value (specifically, an average velocity), the higher brightness in red, and the larger the dispersion, the higher brightness in yellow. In this way, the blood-flow information is expressed in color of a particle, thereby precisely expressing a spatial distribution of a blood flow that has no clear border.

The blood-flow image creating unit 14c can adjust coloring of a particle in accordance with one of "velocity, dispersion, and power", or a combination of some of "velocity, dispersion, and power", and the operator sets which information from among the blood-flow information to be used for coloring of a particle. An adjustment of the color and the brightness of a particle is to be carried out as the image processing apparatus 10 preliminarily stores a look up table in which "velocity, dispersion, and power" are associated with "coloring".

Secondly, the blood-flow image creating unit 14c determines the size of a particle in three-dimensional particle data based on the velocity of a blood flow, and/or the dispersion of velocities of the blood flow, and/or the power of the blood flow.

Precisely, the blood-flow image creating unit 14c varies the sizes of particles in accordance with the blood-flow information (velocity, dispersion, and power), as shown in the section (B) in FIG. 7. For example, the blood-flow image creating unit 14c depicts a blood flow of which velocity is small in absolute value so as to be displayed with a cube of which length of each side is short, and by contrast, a blood flow of which velocity is large in absolute value so as to be displayed with a cube of which length of each side is long. In this way, the blood-flow information is expressed in the size of a particle, thereby precisely expressing a spatial distribution of a blood flow that has no clear border.

The blood-flow image creating unit 14c can adjust the size of a particle in accordance with one of "velocity, dispersion, and power", or a combination of some of "velocity, dispersion, and power", and the operator sets which information from among the blood-flow information to be used for adjusting the size of a particle. An adjustment of the size of a particle is to be carried out as the image processing apparatus 10 preliminarily stores a look up table in which "velocity, dispersion, and power" are associated with "size of particle".

Thirdly, the blood-flow data converting unit 14b determines the arrangement density of particles in three-dimensional particle data based on the velocity of a blood flow, and/or the dispersion of velocities of the blood flow, and/or the power of the blood flow.

Precisely, the blood-flow data converting unit 14b varies the arrangement densities of particles in accordance with the blood-flow information (velocity, dispersion, and power), as shown in the section (C) in FIG. 7. For example, the blood-flow data converting unit 14b determines the arrangement density so as to depict a blood flow of which velocity is small in absolute value with cubes at a small arrangement density, and by contrast, to depict a blood flow of which velocity is large in absolute value with cubes at a large arrangement density. The blood-flow image creating unit 14c then creates a blood-flow image on which particles are scattered at the arrangement density determined by the blood-flow data converting unit 14b. In this way, the blood-flow information is expressed in the arrangement density of particles, thereby precisely expressing a spatial distribution of a blood flow that has no clear border. Furthermore, by varying the arrangement densities of particles in accordance with dispersion, a spatial distribution of a turbulent blood flow that has a border can be more precisely expressed.

The blood-flow data converting unit 14b can adjust the arrangement density of particles in accordance with one of "velocity, dispersion, and power", or a combination of some of "velocity, dispersion, and power", and the operator sets which information from among the blood-flow information to be used for varying the arrangement density of particles. An adjustment of the arrangement density of particles is to be carried out as the image processing apparatus 10 preliminarily stores a look up table in which "velocity, dispersion, and power" are associated with "arrangement density of particles".

Fourthly, the blood-flow data converting unit 14b sequentially creates three-dimensional particle-position change data that the position of a particle to be arranged in three-dimensional particle data is changed with predetermined intervals. The blood-flow image creating unit 14c then sequentially creates a blood-flow image from the sequentially-created three-dimensional particle-position change data, and the composite-image creating unit 14d sequentially creates a composite image by combining a tissue image with the sequentially-created blood-flow image. Three-dimensional particle-position change data corresponds to "three-dimensional particle-position change information" described in the accompanying claims.

For example, as shown in the section (A) in FIG. 8, the blood-flow data converting unit 14b changes the position of a particle to be arranged in the three-dimensional particle data with predetermined intervals (for example, 0.5 second intervals); the blood-flow image creating unit 14c sequentially creates "a blood-flow image 1, a blood-flow image 2, and a blood-flow image 3" with respective pieces of the three-dimensional particle-position change data in which the position of the particle is changed; and the composite-image creating unit 14d sequentially creates "a composite image 1, a composite image 2, and a composite image 3" by combing a tissue image with "the blood-flow image 1, the blood-flow image 2, and the blood-flow image 3" that are sequentially created, respectively.

The display control unit 16 then controls display of "the composite image 1, the composite image 2, and the composite image 3" so as to be sequentially displayed onto the monitor included in the output unit 12. Accordingly, even a steady blood flow (i.e., a blood flow having a steady velocity, dispersion, and power) can be expressed as a state of flowing blood by changing the display position of a cube with time.

Fifthly, the blood-flow data converting unit 14b sequentially creates three-dimensional particle-position change data by changing the position of a particle to be arranged in three-dimensional particle data based on velocity, and/or dispersion. The blood-flow image creating unit 14c then sequentially creates a blood-flow image from the sequentially-created three-dimensional particle-position change data, and the composite-image creating unit 14d sequentially creates a composite image by combining a tissue image with the sequentially-created blood-flow image.

For example, as shown in the section (B) in FIG. 8, the blood-flow data converting unit 14b changes the position of a particle to be arranged in the three-dimensional particle data based on the velocity; the blood-flow image creating unit 14c sequentially creates "a blood-flow image A, a blood-flow image B, and so on" with respective pieces of the three-dimensional particle-position change data in which the position of the particle is changed; and the composite-image creating unit 14d sequentially creates "a composite image A, a composite image B, and so on" by combining a tissue image with "the blood-flow image A, the blood-flow image B, and so on" that are sequentially created, respectively. Precisely, the blood-flow data converting unit 14b changes "the display position of a cube in the current display frame" to "a display position of the cube in the next frame" based on the velocity.

Specifically, a change position of a cube is calculated based on a three-dimensional velocity vector of the blood flow that is actually measured. For example, the blood-flow data converting unit 14b sets "a display position of the cube in the next frame" to a position shifted from the display position in the current frame in the direction of transmitting an ultrasonic wave by a value that the measured velocity is multiplied by a constant (for example, "0.01"). The three-dimensional velocity vector of the blood flow can be expressed by connecting the two points of the positions with a straight line or an arrow.

The display control unit 16 then controls display of "the composite image A, the composite image B, and so on" so as to be sequentially displayed onto the monitor included in the output unit 12. In this way, a cube is shifted by reflecting an actual measurement, so that a composite image on which a shift of the blood flow is accurately reflected can be sequentially displayed.

Processing performed by the image processing apparatus 10 according to the first embodiment is explained below with reference to FIG. 9. FIG. 9 is a flowchart for explaining the processing performed by the image processing apparatus according to the first embodiment.

As shown in FIG. 9, when the image processing apparatus 10 according to the first embodiment receives an display-subject region setting request and an image display request from the operator via the input unit 11 (Yes at Step S901), the tissue-image creating unit 14a converts the coordinate system of three-dimensional tissue data stored by the three-dimensional data storage unit 13 into the rectangular coordinate system (Step S902), and creates a tissue image including depth values by volume rendering from the coordinate-converted three-dimensional tissue data (Step S903).

The blood-flow data converting unit 14b then converts three-dimensional blood-flow data stored by the three-dimensional data storage unit 13 into three-dimensional particle data by scattering a blood flow in the three-dimensional blood-flow data into particles (Step S904), and the blood-flow image creating unit 14c expresses particles in the three-dimensional particle data created by the blood-flow data converting unit 14b in polygon (Step S905).

The blood-flow image creating unit 14c then converts the coordinate system of the three-dimensional particle data into the rectangular coordinate system (Step S906), and creates a blood-flow image including depth values by projecting processing from the coordinate-converted three-dimensional particle data (Step S907).

After that, the composite-image creating unit 14d creates a composite image by coordinating the order of rendering the particles and the tissue based on depth values of pixels included in the tissue image and depth values of particles included in the blood-flow image (Step S908).

The display control unit 16 then controls display of the composite image so as to be displayed in order onto the monitor included in the output unit 12 (Step S909), and then the processing is terminated. Sometimes, the operator of the image processing apparatus 10 performs display of the composite image in a turned manner in an arbitrary direction, in some cases.

When executing particle arrangement-density changing processing based on blood-flow information, the processing is executed by the blood-flow data converting unit 14b at Step S904. Moreover, when executing particle-size changing processing based on blood-flow information, the processing is executed by the blood-flow image creating unit 14c at Step S905. Furthermore, when executing particle-color changing processing based on blood-flow information, the processing is executed by the blood-flow image creating unit 14c at Step S907.

Moreover, particle arrangement-position changing processing explained with reference to FIG. 8 is performed by repeatedly executing the processes from Step S904 to Step S907.

According to the first embodiment, explained above is a case where the blood-flow image creation processing is to be performed after the tissue-image creation processing; however, the present invention is not limited to this, and the tissue-image creation processing can be performed after the blood-flow image creation processing. Alternatively, the tissue-image creation processing can be executed in parallel with the blood-flow image creation processing.

As described above, according to the first embodiment, the tissue-image creating unit 14a creates a tissue image including depth values by volume rendering from three-dimensional tissue data stored by the three-dimensional data storage unit 13; the blood-flow data converting unit 14b converts three-dimensional blood-flow data stored by the three-dimensional data storage unit 13 into three-dimensional particle data by scattering a blood flow in the three-dimensional blood-flow data into particles; and the blood-flow image creating unit 14c creates a blood-flow image including depth values from the three-dimensional particle data.

The composite-image creating unit 14d then creates a composite image by coordinating the order of rendering particles and tissue based on depth values of pixels included in the tissue image and depth values of the particles included in the blood-flow image; the display control unit 16 controls display of the composite image so as to be displayed in order onto the monitor included in the output unit 12. Accordingly, as a blood flow is expressed as particles, even if a three-dimensional blood-flow distribution is displayed in a superposed manner over three-dimensional histology, a blood flow or histology can be avoided from being hidden behind a blood flow in the front, so that a blood flow can be displayed in three dimensions in a format suitable for diagnosis, as described in the main feature. In other words, an operator, such as a doctor, can observe both a blood flow and histology, and can simplify diagnosis.

Not only observing a composite image in a stationary state, but also by turning the composite image in an arbitrary direction, a more stereoscopic blood-flow distribution can be observed, and an operator, such as a doctor, can observe both a blood flow and histology, and can simplify diagnosis.

Figure 10:
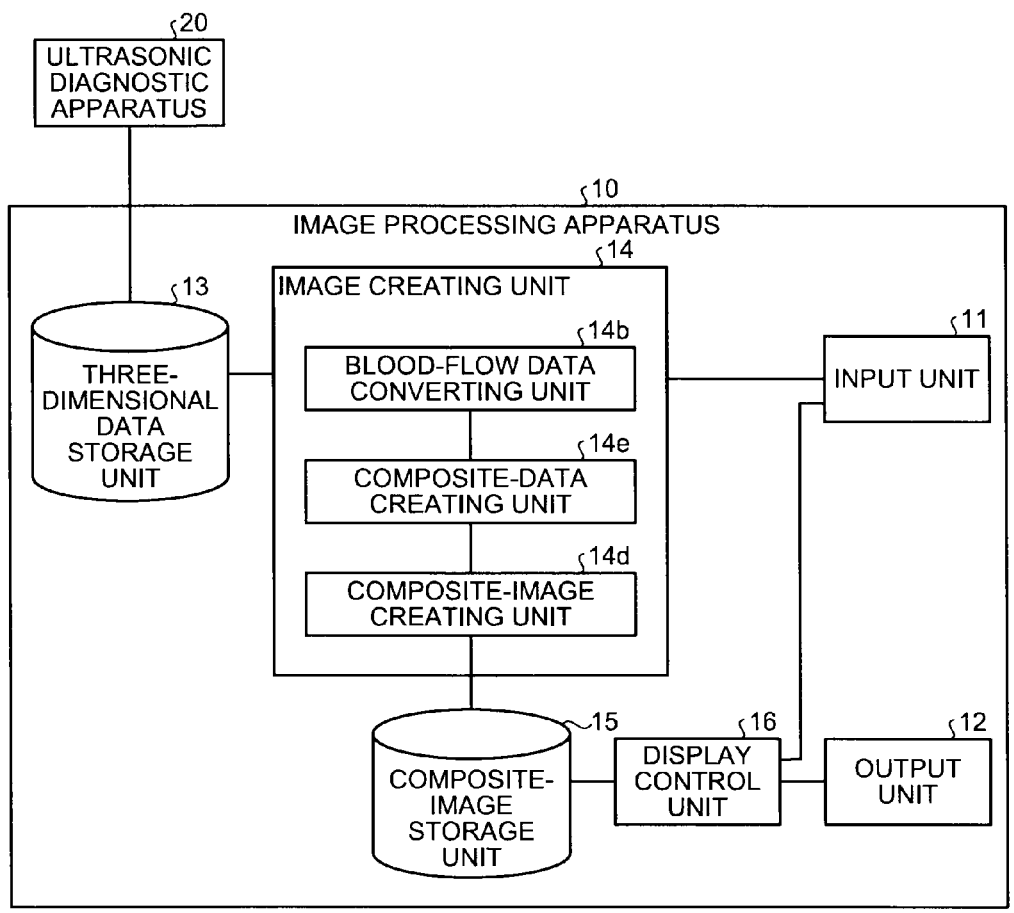
FIG. 10 is a functional block diagram for explaining a configuration of an image processing apparatus according to a second embodiment of the present invention.

The first embodiment is explained above in a case where a composite image is created after a tissue image and a blood-flow image are created. According to a second embodiment of the present invention, a case where a composite image is created at once is explained below with reference to FIG. 10. FIG. 10 is a functional block diagram for explaining a configuration of an image processing apparatus according to the second embodiment.

As shown in FIG. 10, similarly to the image processing apparatus according to the first embodiment, the image processing apparatus 10 according to the second embodiment is connected to the ultrasonic diagnostic apparatus 20, and includes the input unit 11, the output unit 12, the three-dimensional data storage unit 13, the image creating unit 14, the composite-image storage unit 15, and the display control unit 16. However, the image creating unit 14 according to the second embodiment differs from the image creating unit 14 according to the first embodiment, and includes a composite-data creating unit 14e instead of the tissue-image creating unit 14a and the blood-flow image creating unit 14c. The following explanations are described with a focus on the composite-data creating unit 14e.

Similarly to the first embodiment, the blood-flow data converting unit 14b converts three-dimensional blood-flow data stored by the three-dimensional data storage unit 13 into three-dimensional particle data by scattering a blood flow in the three-dimensional blood-flow data into particles.

The composite-data creating unit 14e creates composite data that the three-dimensional particle data created by the blood-flow data converting unit 14b is combined with three-dimensional tissue data stored by the three-dimensional data storage unit 13. When creating the composite data, the composite-data creating unit 14e creates the composite data by giving identification information for identifying the three-dimensional particle information and the three-dimensional histology information. Composite data corresponds to "composite information" described in the accompanying claims.

Specifically, the composite-data creating unit 14e limits an input tone of three-dimensional tissue data between "0 and 200", and limits an input tone of three-dimensional particle data to the tone of "255", and then creates composite data. In other words, by referring to the value of an input tone, data can be identified whether it is derived from three-dimensional tissue data or three-dimensional particle data. The composite-data creating unit 14e creates data that information other than "information about particles to be arranged in three dimensions in a scattered manner" is taken out from the three-dimensional particle data, and then creates composite data.

The composite-image creating unit 14d creates a composite image based on the composite data created by the composite-data creating unit 14e. In other words, the composite-image creating unit 14d converts the coordinate system of the composite data that three-dimensional information about particles representing a blood flow is embedded in three-dimensional information about histology into the rectangular coordinate system, then volume-renders the composite data at once, and then creates a composite image that pieces of information about "histology and a blood flow" are combined. Composite-image creation corresponding is explained below.

Generally, according to volume rendering, a writing content $P_i$ into a frame buffer after rendering "an i-th cross section" is expressed as "$P_i = [1-f(I_i)]P_i-1+g(I_i)$". A function "f" is a transparency function, and a function "g" is a transfer function.

The composite-image creating unit 14d creates a composite image by giving a particular value to a particle representing a blood flow in the transparency function and the transfer function used for volume rendering.

For example, when an input value "$I_i$" is equal to or more than 220 in the composite data, it is considered as a particle representing a blood flow, so that the composite-image creating unit 14d sets the value of the transparency function "$f(I_i)$" to "1", and sets the transfer function to "$g(I_i)=(255, 0, 0)$". Three values in the brackets of the transfer function indicate respective values of Red (R), Green (G), and Blue (B) when coloring in the RGB color mode. Precisely, "$g(I_i)=(255, 0, 0)$" indicates that the color of a particle is expressed in red. By changing the three values in the brackets of the transfer function, processing of changing the color and the brightness of a particle based on blood-flow information can be performed.

Moreover, when the input value "$I_i$" is less than 220 in the composite data, it is considered as data representing histology, so that the composite-image creating unit 14d sets the value of the transparency function "$f(I_i)$" to a value optimal to histology in accordance with the input value, and sets the three values in the brackets of the transfer function to the same value to express the histology in gray scale. Accordingly, similarly to the first embodiment, the composite-image creating unit 14d creates a composite image that depicts histology and a blood flow in three dimensions through one time of volume rendering (see FIG. 6).

The reason why a threshold for determining whether data is derived from three-dimensional tissue data or three-dimensional particle data is not set to "200" but "220" is because it is to perform interpolation processing for expressing a blood flow as particles in a scattered manner.

Figure 11:
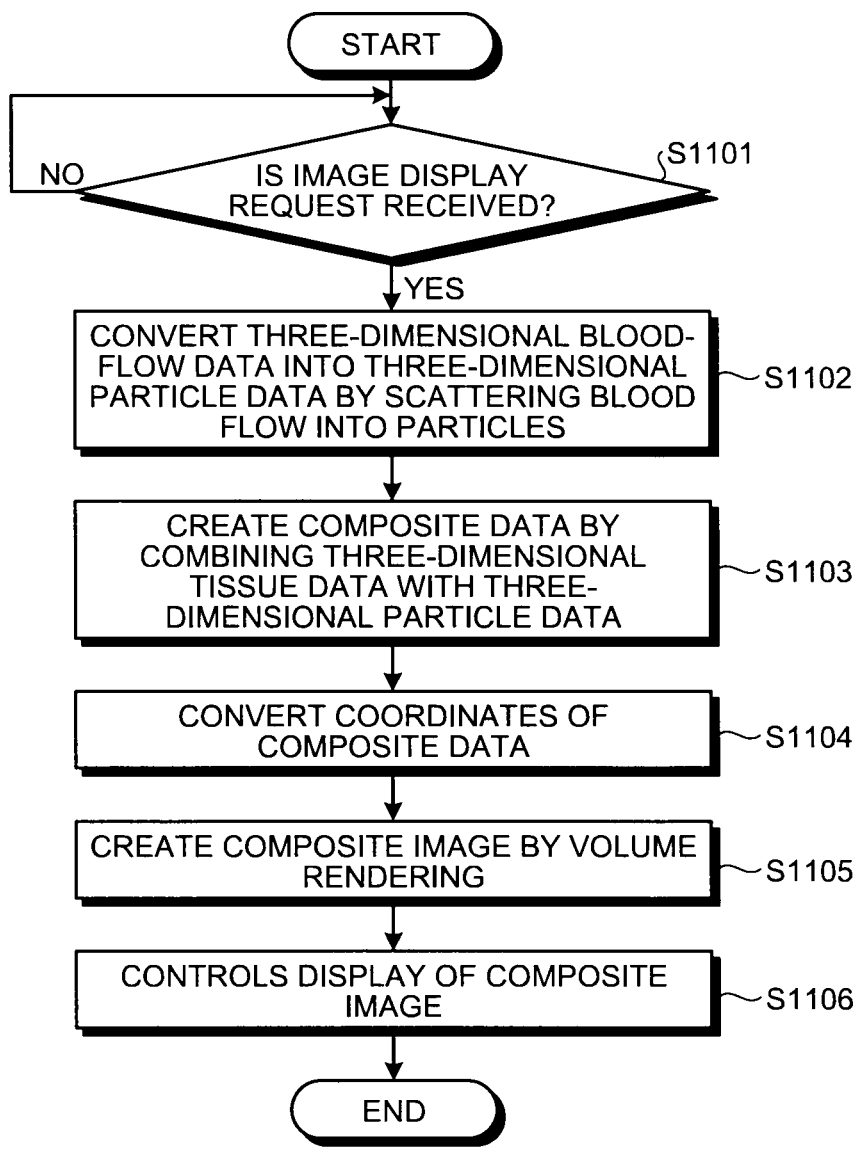
FIG. 11 is a flowchart for explaining processing performed by the image processing apparatus according to the second embodiment.

Processing performed by the image processing apparatus 10 according to the second embodiment is explained below with reference to FIG. 11. FIG. 11 is a flowchart for explaining the processing performed by the image processing apparatus according to the second embodiment.

As shown in FIG. 11, similarly to the first embodiments, when the image processing apparatus 10 according to the second embodiment receives a display-subject region setting request and an image display request from the operator via the input unit 11 (Yes at Step S1101), the blood-flow data converting unit 14b converts three-dimensional blood-flow data stored by the three-dimensional data storage unit 13 into three-dimensional particle data by scattering a blood flow in the three-dimensional blood-flow data into particles (Step S1102).

The composite-data creating unit 14e then creates composite data that the three-dimensional particle data created by the blood-flow data converting unit 14b is combined with three-dimensional tissue data stored by the three-dimensional data storage unit 13, by limiting an input tone (Step S1103).

The composite-image creating unit 14d then converts the coordinate system of the composite data created by the composite-data creating unit 14e into the rectangular coordinate system (Step S1104), and then creates a composite image by volume rendering (Step S1105).

The display control unit 16 then controls display of the composite image so as to be displayed in order onto the monitor included in the output unit 12 (Step S1106), and then the processing is terminated.

As described above, according to the second embodiment, a composite image can be created through one time of volume rendering, so that display processing of the composite image can be quickly performed.

Although the first embodiment is explained above in a case where three-dimensional tissue data is displayed by creating a three-dimensional image by volume rendering, the present invention is not limited to this, and can be applied to a case of creating and displaying a cross-sectional tissue image corresponding to a certain cross section in the three-dimensional tissue data.

Sometimes histology of a portion other than the heart and an embryo (for example, a tumor portion in the liver) cannot be expressed precisely in three-dimensional structure by volume rendering in some cases. In such case, the use of a Multi Planar Reformat (MPR) image is suitable as an image that depicts histology.

The tissue-image creating unit 14a creates an MPR image corresponding to a cross section received from the operator of the image processing apparatus 10 via the input unit 11 based on three-dimensional tissue data; and the composite-image creating unit 14d creates a composite image that the MPR image created by the tissue-image creating unit 14a is combined with a blood-flow image created by the blood-flow image creating unit 14c, after aligning the positions inside the subject. The display control unit 16 then controls display of the created composite image so as to be displayed onto the monitor included in the output unit 12.

In this way, by creating and displaying a composite image that an MPR image is combined with a blood-flow image, even when displaying a blood flow and a tissue portion of which three-dimensional structure cannot be precisely expressed by volume rendering, the blood flow can be expressed in three dimensions in a format suitable for diagnosis.

When using an MPR image as described above, similarly to the first embodiment, superposition in the depth direction of a tissue and a blood flow expressed in particles is determined by using depth values of the MPR image and the blood-flow image, and a composite image is then created by coordinating so as to render priorly a particle or a tissue that is located in front. Alternatively, a composite image of which transparency is increased can be created.

Figure 12:
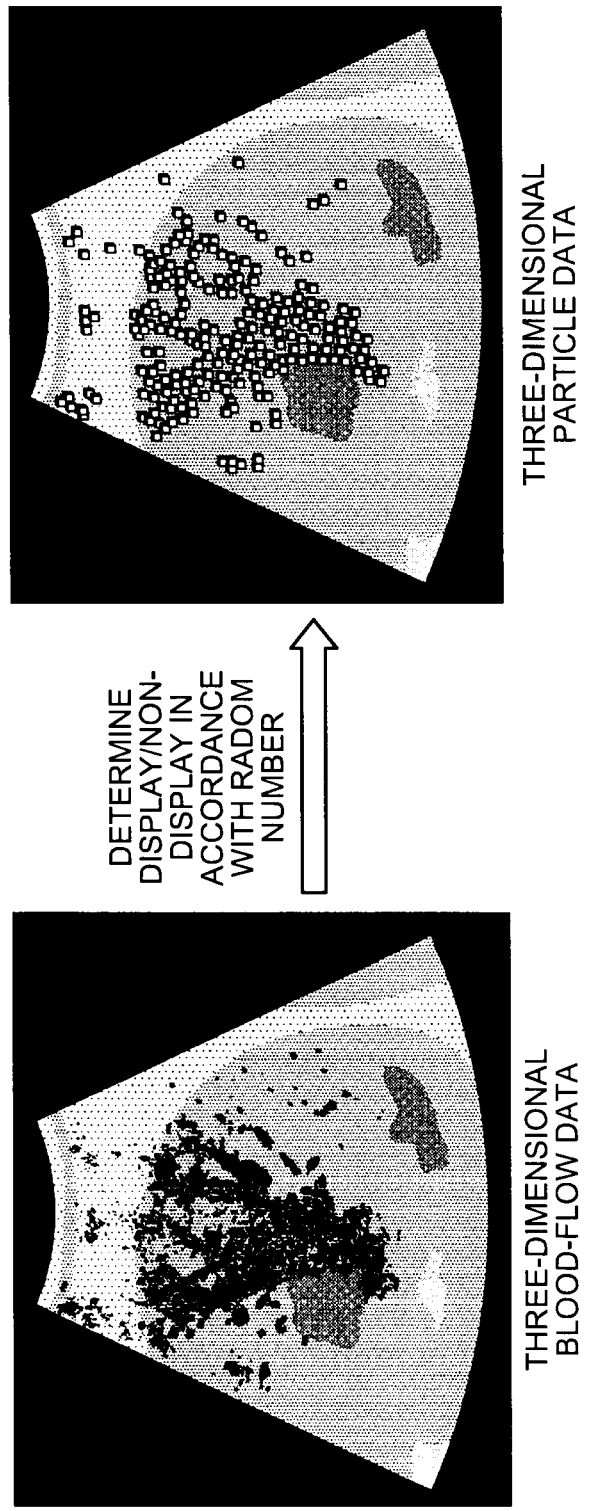
FIG. 12 is a schematic diagram for explaining a method of creating three-dimensional particle data according to a third embodiment of the present invention.

According to a third embodiment of the present invention, a case where three-dimensional particle data is created from three-dimensional blood-flow data by a method different from the first and second embodiments is explained below with reference to FIGS. 12 and 13. FIG. 12 is a schematic diagram for explaining a method of creating three-dimensional particle data according to the third embodiment; and FIG. 13 is a schematic diagram for explaining a composite-image creating unit according to the third embodiment.

A method explained below of creating three-dimensional particle data by the image processing apparatus 10 according to the third embodiment can be applied to both the blood-flow data converting unit 14b of the image processing apparatus 10 according to the first embodiment explained above with reference to FIG. 2, and the blood-flow data converting unit 14b of the image processing apparatus 10 according to the second embodiment explained above with reference to FIG. 10.

According to the first and second embodiments, three-dimensional particle data is created by arranging particles in a scattered manner in an area in which a blood flow is present in three-dimensional blood-flow data. However, according to the third embodiment, three-dimensional particle data is created by removing an area in which a blood flow is present in three-dimensional blood-flow data with certain intervals.

Specifically, as shown in FIG. 12, the blood-flow data converting unit 14b according to the third embodiment determines whether or not to display (display/non-display) three-dimensional blood-flow data (three-dimensional information about a blood flow having depth) on each pixel of a composite image in accordance with random numbers that spatially and temporally vary.

By determining display/non-display by using random numbers that spatially and temporally vary, the blood-flow data converting unit 14b according to the third embodiment creates three-dimensional particle data converted with scattered particles from the three-dimensional blood-flow data, similarly to the three-dimensional particle data explained in the first and second embodiments. Moreover, by using random numbers that vary not only spatially but also temporally, the blood-flow data converting unit 14b according to the third embodiment creates the three-dimensional particle data that particles shift along time sequence.

The shape of a particle to be arranged onto a pixel determined to be displayed can be a cube in shape as shown in FIG. 12; however, the present invention is not limited to this, and an arbitrary shape, for example, a sphere, can be set by the operator.

Furthermore, similarly to the first or second embodiment, the blood-flow data converting unit 14b according to the third embodiment can create three-dimensional particle data such that colors of particles, and/or arrangement densities of the particles, and/or sizes of the particles vary in accordance with the velocity of a blood flow, and/or the dispersion of velocities of the blood flow, and/or the power of the blood flow.

The three-dimensional particle data created by the blood-flow data converting unit 14b is then combined with a tissue image to compose a composite image through the processing explained in the first or second embodiment. In other words, when applying the third embodiment to the first embodiment, the blood-flow image creating unit 14c creates a blood-flow image including depth values from three-dimensional particle data created by the blood-flow data converting unit 14b, and the composite-image creating unit 14d creates a composite image by coordinating the order of rendering particles and tissue based on depth values of pixels included in a tissue image and the depth values of pixels included in the blood-flow image.

Alternatively, when applying the third embodiment to the second embodiment, the composite-data creating unit 14e creates composite data that three-dimensional particle data created by the blood-flow data converting unit 14b is combined with three-dimensional tissue data, and the composite-image creating unit 14d creates a composite image through one time processing of volume rendering on the composite data.

For example, when three-dimensional particle data is created four times per second in accordance with random numbers varying with quarter-second intervals, as shown in FIG. 13, the composite-image creating unit 14d according to the third embodiment creates a composite image from three-dimensional blood-flow data at the first one time (t=0), and then creates composite images from three-dimensional particle data in the other three times (t=¼, 2/4, and ¾). Accordingly, the monitor of the output unit 12 displays a total image of a blood flow at first, and then displays a composite image on which a tissue image hidden behind the blood flow can be observed. FIGS. 12 and 13 depict composite images of an MPR image of tissue in a kidney and blood-flow images.

As described above, according to the third embodiment, because three-dimensional particle data is created only by removing part of the three-dimensional blood-flow data with random numbers, a composite image on which a blood-flow distribution and histology can be both observed can be easily created.

Moreover, according to the third embodiment, by varying random numbers spatially and temporally, a composite image that can depict a state of flowing blood can be created, for example, even from a static image created through one time of a scan with ultrasonic wave. Furthermore, according to the third embodiment, a stereoscopic effect of the blood flow in the composite image can be improved by controlling the generation of random numbers such that the more front in three dimensions the blood flow, the higher density the particles are to be displayed at.

Moreover, according to the third embodiment, because three-dimensional blood-flow data becomes a composite subject to be combined with three-dimensional tissue data with certain intervals, it is achievable that a doctor who performs image diagnosis can refer to a composite image on which a blood-flow distribution and histology can be observed at once meanwhile a total image of the blood flow is still retained as persistence of vision, thereby performing an accurate diagnosis.

According to each of the first to third embodiments, explained above is a case where the image processing apparatus 10 is provided separately from the ultrasonic diagnostic apparatus 20; however, the present invention is not limited to this, and the ultrasonic diagnostic apparatus 20 can include the functions of the image processing apparatus 10.

Moreover, according to each of the first to third embodiments, explained above is a case where the image processing apparatus 10 acquires and processes three-dimensional tissue data and three-dimensional blood-flow data from the ultrasonic diagnostic apparatus 20; however, the present invention is not limited to this, the image processing apparatus 10 can acquire and process three-dimensional tissue data and three-dimensional blood-flow data from a medical-image database that stores data created by a medial-image diagnostic apparatus, such as the ultrasonic diagnostic apparatus 20.

The components of each device shown in the drawings are conceptual for describing functions, and not necessarily to be physically configured as shown in the drawings. In other words, concrete forms of distribution and integration of the units are not limited to those shown in the drawings, and all or part of the units can be configured to be functionally or physically distributed and integrated in an arbitrary unit depending on various loads and conditions in use. Furthermore, all or an arbitrary part of processing functions performed by the respective units can be implemented by a Central Processing Unit (CPU) and a computer program to be executed by the CPU, or can be implemented as hardware by wired logic.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus, comprising:
a processing circuit configured to
acquire three-dimensional histology information about tissue inside a subject and three-dimensional fluid information about fluid moving inside the subject, both of which are created based on a reflection wave of an ultrasonic wave transmitted to an inside of the subject,
create three-dimensional particle information by removing an area in which the fluid is present in the three-dimensional fluid information at designated spatial intervals in order to replace a portion of flow data within the three-dimensional fluid information with a plurality of scattered, sparsely-distributed particles in three dimensions, each particle being represented by a graphical symbol having a predetermined shape,
create a composite image based on the created three-dimensional particle information and the three-dimensional histology information, and
control display of the composite image so that the composite image is displayed on a predetermined display.

2. The image processing apparatus according to claim 1, wherein the processing circuit is further configured to create the composite image by rendering a foreground of a particle or a tissue, based on positional information in three dimensions about the particles in the three-dimensional particle information, and positional information in three dimensions about the tissue in the three-dimensional histology information.

3. The image processing apparatus according to claim 1, wherein the processing circuit is further configured to create composite information that the three-dimensional fluid information is combined with the three-dimensional histology information by giving identification information for identifying the three-dimensional fluid information and the three-dimensional histology information, and to create the composite image based on created composite information.

4. The image processing apparatus according to claim 1, wherein
the processing circuit is further configured to sequentially create three-dimensional particle-position change information indicating positions in the three-dimensional particle information at which the particles are to be arranged are changed with predetermined time intervals, and to sequentially create the composite image based on the sequentially-created three-dimensional particle-position change information and the three-dimensional histology information; and
the processing circuit is further configured to control display of the composite image sequentially created by the processing circuit so as to be sequentially displayed onto the predetermined display.

5. The image processing apparatus according to claim 4, wherein the processing circuit is further configured to sequentially create the three-dimensional particle-position change information by changing positions at which the particles are to be arranged, based on at least one of a velocity of the fluid and a dispersion of velocities of the fluid.

6. The image processing apparatus according to claim 1, wherein
the processing circuit is further configured to create a cross-sectional tissue image corresponding to a specified cross section in the three-dimensional histology information, and to create a composite image combining the created cross-sectional tissue image and an image created by using the three-dimensional particle information in both of which positions inside the subject are aligned with each other; and
the processing circuit is further configured to control display of the composite image created by the processing circuit so as to be displayed on the predetermined display.

7. The image processing apparatus according to claim 1, wherein the processing circuit is further configured to change the designated spatial intervals along a time sequence.

8. The image processing apparatus according to claim 7, wherein the processing circuit is further configured to take the three-dimensional fluid information with certain time intervals as a composition subject to be combined with the three-dimensional histology information.

9. The image processing apparatus of claim 1, wherein the processing circuit is further configured to divide the area in which the fluid is present into cubes of a predetermined size, and to arrange each of the plurality of particles within corresponding selected cubes, wherein a size of each particle is smaller than the predetermined size of each of the cubes.

10. The image processing apparatus of claim 1, wherein the processing circuit is further configured to determine at least one of a color of each of the particles, an arrangement density of the particles, and a size of each of the particles, based on at least one of a velocity of the fluid, a dispersion of velocities of the fluid, and a diffusion strength of the fluid.

11. A non-transitory computer-readable medium storing programmed instructions for processing an image, wherein the instructions, when executed by a computer, cause the computer to perform a method comprising:
acquiring three-dimensional histology information about tissue inside a subject and three-dimensional fluid information about fluid moving inside the subject;
creating three-dimensional particle information by removing an area in which the fluid is present in the three-dimensional fluid information at designated spatial intervals in order to replace a portion of flow data within the three-dimensional fluid information with a plurality of scattered, sparsely distributed particles in three dimensions, each particle being represented by a graphical symbol having a predetermined shape;
creating a composite image based on the created three-dimensional particle information and the three-dimensional histology information; and
controlling display of the composite image so that the composite image is displayed on a predetermined display.

* * * * *